United States Patent
Kano et al.

(10) Patent No.: US 10,662,449 B2
(45) Date of Patent: May 26, 2020

(54) METHOD FOR PRODUCING COMPOUND AND COMPOUND PRODUCTION SYSTEM USED IN PRODUCTION METHOD

(71) Applicants: Mitsubishi Chemical Corporation, Tokyo (JP); Mitsubishi Chemical Engineering Corporation, Chuo-ku (JP)

(72) Inventors: Makoto Kano, Yokohama (JP); Takamitsu Kariya, Yokohama (JP); Hiroyasu Banba, Yokohama (JP); Tomohiko Mawatari, Yokohama (JP); Takeshi Kato, Otake (JP); Tsutomu Hirachi, Tokyo (JP); Keizo Tachibana, Yokohama (JP); Masahiro Kamide, Toyohashi (JP); Megumu Morimoto, Tokyo (JP)

(73) Assignees: Mitsubishi Chemical Corporation, Tokyo (JP); Mitsubishi Chemical Engineering Corporation, Chuo-ku (JP)

( * ) Notice: Subject to any disclaimer, the term of this patent is extended or adjusted under 35 U.S.C. 154(b) by 0 days.

(21) Appl. No.: 15/311,794

(22) PCT Filed: Jul. 3, 2015

(86) PCT No.: PCT/JP2015/069307
§ 371 (c)(1),
(2) Date: Nov. 16, 2016

(87) PCT Pub. No.: WO2016/006556
PCT Pub. Date: Jan. 14, 2016

(65) Prior Publication Data
US 2018/0119186 A1  May 3, 2018

(30) Foreign Application Priority Data
Jul. 10, 2014 (JP) ................................ 2014-142688

(51) Int. Cl.
*C12P 13/02* (2006.01)
*C12M 1/02* (2006.01)
*C12M 1/00* (2006.01)
*C12M 1/06* (2006.01)

(52) U.S. Cl.
CPC ............... *C12P 13/02* (2013.01); *C12M 1/02* (2013.01); *C12M 23/58* (2013.01); *C12M 27/02* (2013.01)

(58) Field of Classification Search
None
See application file for complete search history.

(56) References Cited

U.S. PATENT DOCUMENTS

| | | | | |
|---|---|---|---|---|
| 3,709,641 A | * | 1/1973 | Sarem | B01J 4/02 425/67 |
| 2009/0035856 A1 | * | 2/2009 | Galliher | C12M 23/14 435/383 |
| 2011/0021819 A1 | | 1/2011 | Kanou et al. | |
| 2012/0276601 A1 | | 11/2012 | Kariya et al. | |
| 2013/0180165 A1 | * | 7/2013 | Brasil | B01J 19/10 44/639 |
| 2014/0134683 A1 | | 5/2014 | Kanou et al. | |

FOREIGN PATENT DOCUMENTS

| | | | |
|---|---|---|---|
| JP | 2004283128 A | * | 10/2004 |
| JP | 2012/527243 | | 11/2012 |
| JP | 2014-113092 | | 6/2014 |
| RU | 2112804 C1 | * | 6/1998 |
| WO | 89/06273 | | 7/1989 |
| WO | WO 2009/113654 A1 | | 9/2009 |
| WO | 2010/135365 | | 11/2010 |
| WO | WO 2011/078184 A1 | | 6/2011 |
| WO | 2012/116394 | | 9/2012 |

OTHER PUBLICATIONS

EngMT. Katsuo, I. et al. Method for producing high-quality (meth)acrylamide polymer using biocatalyst. Japanese Patent Application No. JP2004-283128(A), Oct. 14, 2004. pp. 1-12. specif. pp. 2, 3, 5, 6, 9, 10.*
EngMT. Kuzmitsky, G.E. et al. A biotechnological preparation method of concentrated acrylamide solutions. Russian Patent Application No. RU 2112804, Aug. 27, 1998. pp. 1-7. specif. pp. 1, 5.*
Australian Office Action dated Jun. 27, 2018 in Patent Application No. 2018200574, 4 pages.
International Search Report dated Oct. 6, 2015 in PCT/JP2015/069307 (with English language translation).
Michio Fukatsu, et al., "Catalytic technologies for production of acrylonitrile and acrylamide" JETI, vol. 53, No. 5, 2005, pp. 49-51 and 126.
Exhibit A: "Chemical Engineering Handbook" published by Maruzen Co.. Ltd., 1999, pp. 422 and 425 (with a partial translation).
Office Action dated Jan. 14, 2019, in Chinese patent application No. 201580033305.5, with English translation (18 pages).
Li et al, "Microbial Conversion of Acrylonitrile to Acrylamide; Bacteria Screening and Microbial Conversion of Acrylonitrile", *Acta Microbiologica Sinica*, 1990, vol. 30, No. 1, pp. 29-35—with English abstract (7 pages).

(Continued)

*Primary Examiner* — Renee Claytor
*Assistant Examiner* — Sharon M. Papciak
(74) *Attorney, Agent, or Firm* — Oblon, McClelland, Maier & Neustadt, L.L.P.

(57) ABSTRACT

This method for producing a compound uses a continuous tank reactor which is provided with two or more reaction tanks for producing the compound and with a reaction liquid feeding pipe that feeds a reaction liquid from an upstream reaction tank to a downstream reaction tank, said method being characterized in that the Reynold's number of the reaction liquid that flows in the reaction liquid feeding pipe is configured to be 1800-22000. Furthermore, this compound production system is used in said method for producing a compound, and is formed by housing at least one of the reaction tanks in a portable container.

9 Claims, 2 Drawing Sheets

(56) References Cited

OTHER PUBLICATIONS

Office Action as received in the corresponding Japanese Patent Application No. 2015-535622 dated Oct. 1, 2019 w/Machine translation obtained by Global Dossier on Oct. 31, 2019, 14, pages.
Office Action as received in the corresponding CH Application No. 201580033305.05 dated Jul. 10, 2019 W/English Translation.
Xu Guo-Xu-Xu, Chemical Principle Experiment, "Chapter 5 Demonstration Experiment of Chemical Engineering Principle" published on Sep. 30, 2006, Nanjing University Press w/English Translation.
Office Action as received in the corresponding Japanese Patent Application No. 2015-535622 dated May 7, 2019 w/English translation.
Office Action as received in the corresponding CN Patent Application No. 201580033305.5 dated Dec. 11, 2019, 5 pages.
Office Action as received in the corresponding IN Patent Application No. 201647039307 w/Computer Generated English Translation, dated Jan. 15, 2020, 27 pages.
Office Action as received in the corresponding BR Patent Application No. BR112016026871-7 dated Dec. 24, 2019 w/English Translation.

* cited by examiner

METHOD FOR PRODUCING COMPOUND AND COMPOUND PRODUCTION SYSTEM USED IN PRODUCTION METHOD

TECHNICAL FIELD

The present invention relates to a method for producing a compound and a compound production system used in the production method.

The present application claims priority based on Japanese Patent Application No. 2014-142688, filed Jul. 10, 2014. The contents of the application are incorporated herein by reference in their entirety.

BACKGROUND ART

A method for producing a target compound using a biocatalyst has advantages that reaction conditions are mild, a purity level of a reaction product is high with fewer byproducts, and a production process can be simplified. Therefore, such a method is used for producing various compounds. For example, in production of an amide compound such as acrylamide, since a nitrile hydratase, which is an enzyme for converting a nitrile compound such as acrylonitrile into an amide compound, is found, production of an amide compound using the enzyme has been widely conducted.

Further, in recent years, production of acrylamide by continuous reaction using a nitrile hydratase has been conducted. As an example of methods for producing acrylamide by continuous reaction, there is mentioned a method for producing acrylamide described in Patent Publication 1 which is intended to achieve low costs, energy saving, and low environmental loads. In Patent Publication 1, it is described that, in production of acrylamide by continuous reaction using a nitrile hydratase, enzyme reaction is performed under the conditions of a predetermined stirring power and a predetermined Froude number.

CITATION LIST

Patent Publication

Patent Publication 1: WO 09/113654 A

SUMMARY OF THE INVENTION

Problem to be Solved by the Invention

From the viewpoint of space limitation that is a general problem, also in production of acrylamide by continuous reaction using a nitrile hydratase, it is further desired that space saving is achieved by improving production efficiency.

In this regard, an object of the invention is to provide a method for producing a compound using continuous reaction in which space saving is achieved by improving production efficiency (without a decrease in production efficiency).

Means for Solving Problem

The present inventors have conducted intensive studies, and as a result, they found out that when a Reynolds number of a reaction liquid flowing in a reaction liquid feeding pipe is set to be in a predetermined range, the above-described problem can be solved, thereby completing the invention.

That is, the invention includes the following configurations.

[1] A method for producing a compound using a continuous tank reactor which is provided with two or more reaction tanks for producing a compound and a reaction liquid feeding pipe that feeds a reaction liquid from an upstream reaction tank to a downstream reaction tank, in which a Reynolds number of the reaction liquid flowing in the reaction liquid feeding pipe is set to 1800 to 22000.

[2] A compound production system being used in the method for producing a compound described in [1], in which at least one tank of the reaction tanks is accommodated in a portable container.

[3] The compound production system described in [2], in which when at least one tank of the reaction tanks is accommodated in the portable container, a total volume of the at least one tank of the reaction tanks accommodated in the portable container is 1/6 to 3/5 of an inner volume of the portable container.

[4] The method for producing a compound described in [1], in which the method uses the compound production system described in [2], and a value obtained by dividing an inner volume ($m^3$) of the portable container by a flow rate ($m^3$/hour) of the reaction liquid flowing in the reaction tank accommodated in the portable container is 5 to 70 hours.

[5] The compound production system described in [2] or [3], in which another portable container is disposed on the portable container in which the reaction tank is accommodated.

[6] A method for producing acrylamide using the method for producing a compound described in [1], the acrylamide production method including: a step of supplying an acrylonitrile-containing liquid to at least one tank of the reaction tanks; a step of supplying raw water to at least one tank of the reaction tanks; and a step of supplying a biocatalyst aqueous dispersion to at least one tank of the reaction tanks.

[7] The compound production system described in [2], in which a volume of the reaction tank accommodated in the portable container is 6.4 $m^3$ to 22.9 $m^3$.

[8] The compound production system described in [2], in which the compound is an amide compound.

[9] The compound production system described in [2], in which the compound is acrylamide.

Effect of the Invention

According to the invention, it is possible to provide a method for producing a compound using continuous reaction in which space saving is achieved without a decrease in production efficiency. In addition, a production system of the invention can be carried to a place in which there is a demand for using the production system and can start industrial production of a compound in a short time.

MODE(S) FOR CARRYING OUT THE INVENTION

Embodiment of Method for Producing Compound

Hereinafter, as an embodiment of a method for producing a compound of the invention, an embodiment in which acrylamide is produced using a continuous tank reactor 1 by hydration of acrylonitrile serving as a raw material in the presence of a biocatalyst will be described by means of FIG. 1.

[Continuous Tank Reactor]

Figure 1:
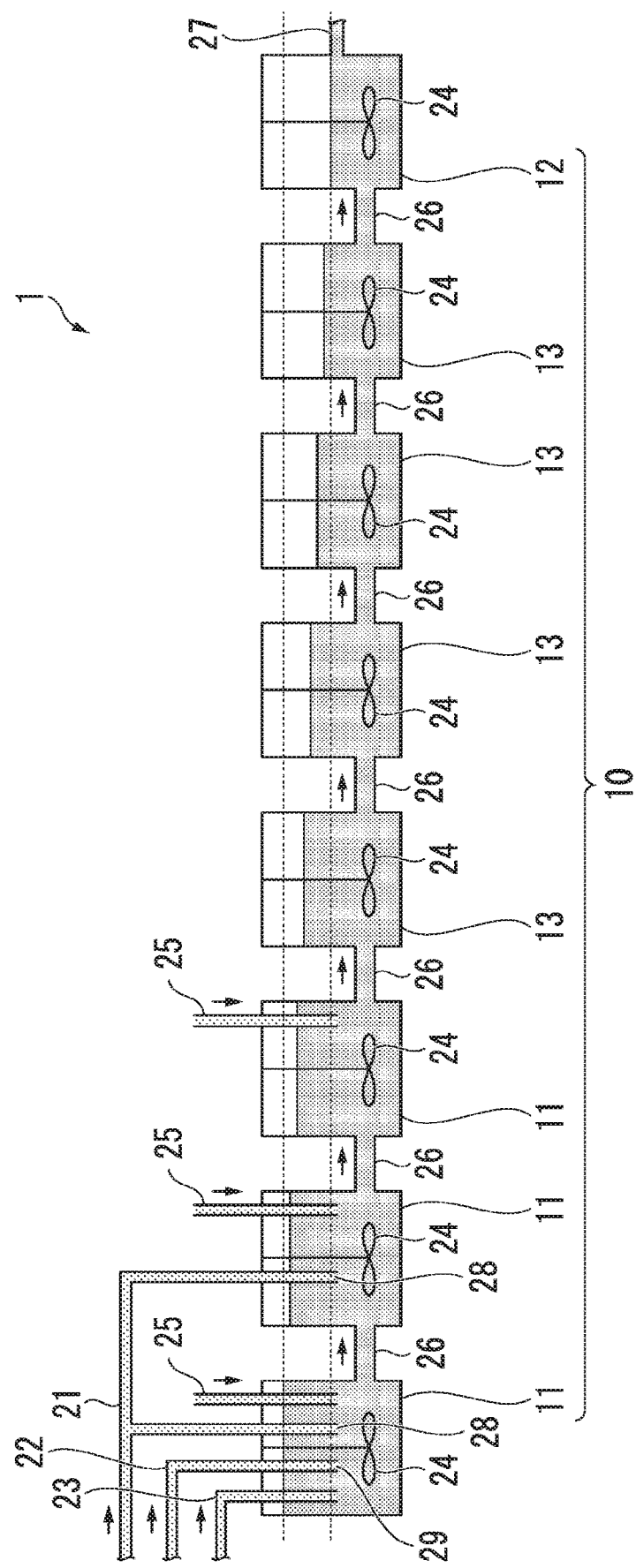
FIG. 1 is a schematic cross-sectional view illustrating an embodiment of a continuous tank reactor used in a method for producing a compound of the invention.

The continuous tank reactor 1 illustrated in FIG. 1 is provided with eight reaction tanks 10 for producing a compound. In addition, the continuous tank reactor 1 is provided with an acrylonitrile supplying pipe 21 supplying an acrylonitrile-containing liquid to the reaction tank 10, a catalyst supplying pipe 22 supplying a biocatalyst aqueous dispersion to the reaction tank 10, and a raw water supplying pipe 23 supplying raw water to the reaction tank 10. Furthermore, the continuous tank reactor 1 may be provided with an acid/alkali solution supplying pipe 25 supplying acid or alkali in order to control a pH of the reaction liquid in the reaction tank 10.

Furthermore, the continuous tank reactor 1 is provided with a stirring blade 24 stirring the reaction liquid obtained by mixing the acrylonitrile-containing liquid, the biocatalyst aqueous dispersion, and the raw water. Furthermore, the continuous tank reactor 1 is provided with a reaction liquid feeding pipe 26 feeding the reaction liquid from the upstream reaction tank to the downstream reaction tank among the reaction tanks 10. Furthermore, the continuous tank reactor 1 is provided with a reaction product collecting pipe 27 collecting an acrylamide-containing aqueous solution from the most downstream reaction tank among the reaction tanks 10.

Liquid feeding in the reaction liquid feeding pipe 26 and the reaction product collecting pipe 27 may be performed by using potential energy generated by a difference between a height of the liquid surface of the upstream reaction tank and a height of the liquid surface of the downstream reaction tank (hereinafter, simply referred to as "liquid surface difference") or may be performed by using pressure energy generated by a liquid feeding pump. From the viewpoint of achieving simplification of the continuous tank reactor 1 and energy saving in production, liquid feeding is preferably performed by using potential energy.

Hereinafter, each configuration of the continuous tank reactor 1 will be described in detail.

(Reaction Tank)

The reaction tanks 10 are further classified into a reaction tank 11 provided with at least one pipe of the acrylonitrile supplying pipe 21, the catalyst supplying pipe 22, the raw water supplying pipe 23, and the acid/alkali solution supplying pipe 25; a reaction tank 12 provided with the reaction product collecting pipe 27; and a reaction tank 13 not provided with any pipe of these pipes. The reaction tank 11 is typically positioned at the upstream side of the flow of the reaction liquid. Further, the reaction tank 12 is typically positioned at the downstream side of the flow of the reaction liquid and is preferably positioned at the most downstream side. Furthermore, the reaction tank 13 may be provided in a case where the reaction tanks 10 are three or more, and in the case of providing the reaction tank 13, the reaction tank 13 is typically positioned between the reaction tank 11 and the reaction tank 12 in the flow of the reaction liquid.

Incidentally, the reaction tank 10 may be provided with a liquid surface sensor measuring the liquid surface of the reaction liquid in the tank.

Further, each reaction tank of the reaction tanks 10 may be an independent reaction tank, or may be a reaction tank obtained by dividing a larger reaction tank with a partition. In a case where each reaction tank is a reaction tank divided with a partition, in this embodiment, each space divided with a partition is counted as one tank.

Further, the reaction tanks 10 are two or more, and all the reaction tanks may be connected with one another. The reaction tanks 10 may be configured such that at least some reaction tank may be connected in series or a reaction tank to be connected in parallel may be provided.

The material of the reaction tank 10 is not particularly limited as long as it is not corroded by the reaction liquid, and stainless steel or the like is preferable.

The shape of the reaction tank 10 is not particularly limited as long as the reaction liquid in the reaction tank is stirred by the stirring blade 24, and for example, a cube shape, a cuboid shape, a cylindrical shape, and the like are mentioned.

The volume of the reaction tank 10 is not particularly limited and can be appropriately selected depending on the scale or the like of the continuous tank reactor 1. For example, in a case where the reaction tank is accommodated in the portable container and used, the volume of the reaction tank as described later can be selected. The shape and volume of the reaction tank 10 are preferably set such that each tank or two or more tanks can be accommodated in the portable container.

In a case where the production of the aqueous solution of acrylamide is performed by continuous reaction, the aqueous solution of acrylamide is produced in a continuous manner without collecting the entire reaction mixture in the reaction vessel while maintaining continuous or intermittent introduction of raw materials for reaction (for example, containing the biocatalyst aqueous dispersion, the raw water, and the acrylonitrile-containing liquid) to the reaction vessel and continuous or intermittent retrieval of the reaction mixture (for example, containing the produced acrylamide) from the reaction vessel.

(Acrylonitrile Supplying Pipe and Raw Water Supplying Pipe)

In this embodiment, a step of supplying the acrylonitrile-containing liquid to the reaction tank and a step of supplying the raw water to the reaction tank are included. These steps are performed by using the acrylonitrile supplying pipe 21 and the raw water supplying pipe 23, respectively.

The material of the acrylonitrile supplying pipe 21 is not particularly limited as long as it is not corroded by the acrylonitrile-containing liquid. The material of the acrylonitrile supplying pipe 21 is preferably, for example, stainless steel or the like.

The inner diameter of the acrylonitrile supplying pipe 21 is preferably 1 to 5 cm. When the inner diameter of the acrylonitrile supplying pipe 21 is equal to or more than the lower limit, the acrylonitrile-containing liquid can be efficiently supplied. On the other hand, when the inner diameter thereof is equal to or less than the upper limit, space saving is further achieved.

The inner diameter of the raw water supplying pipe 23 is preferably 2 to 10 cm. When the inner diameter of the raw water supplying pipe 23 is equal to or more than the lower limit, pressure loss in the raw water supplying pipe 23 can be decreased. On the other hand, when the inner diameter thereof is equal to or less than the upper limit, space saving is further achieved.

In order to control the production quantity of acrylamide, it is preferable that the acrylonitrile supplying pipe 21 and the raw water supplying pipe 23 each have an acrylonitrile supply flow rate adjustment means (for example, an acrylonitrile supply flow rate adjustment unit) and a raw water supply flow rate adjustment means (for example, a raw water supply flow rate adjustment unit). As these adjustment means, a method using a flow rate adjustment valve (for example, a unit having a flow rate adjustment valve), a method controlling power of the liquid feeding pump (for example, a unit controlling power of the liquid feeding pump), and the like are mentioned. The schemes of these adjustment means may be schemes that perform automatic control such that the flow rate of the aqueous solution of acrylamide flowing out from the reaction product collecting pipe 27 by overflow is set to be in cooperation with these adjustment means so that the flow rate of the aqueous solution of acrylamide flowing out from the reaction product collecting pipe 27 is adjusted to a predetermined range.

An acrylonitrile supply port 28 in the acrylonitrile supplying pipe 21 is preferably positioned in the vicinity of the stirring blade 24 in order that the concentration of acrylonitrile in the reaction tank 11 is not partially increased.

(Catalyst Supplying Pipe)

In this embodiment, a step of supplying the biocatalyst aqueous dispersion to the reaction tank is included. The step is performed by using the catalyst supplying pipe 22.

The material of the catalyst supplying pipe 22 is not particularly limited as long as it is not corroded by the biocatalyst aqueous dispersion. The material of the catalyst supplying pipe 22 is preferably, for example, stainless steel or the like.

The inner diameter of the catalyst supplying pipe 22 is preferably 0.4 to 3 cm. When the inner diameter of the catalyst supplying pipe 22 is equal to or more than the lower limit, inactivation of enzymes over time caused by long-term retention of the biocatalyst in the pipe can be suppressed. On the other hand, when the inner diameter thereof is equal to or less than the upper limit, space saving is further achieved. It is preferable that the catalyst supplying pipe 22 has a catalyst supply flow rate adjustment means in order to control the reaction rate from acrylonitrile to acrylamide. As the catalyst supply flow rate adjustment means (for example, a catalyst supply flow rate adjustment unit), a method using a flow rate adjustment valve (a unit having a flow rate adjustment valve), a method controlling power of the liquid feeding pump (for example, a unit controlling power of the liquid feeding pump), and the like are mentioned. The scheme of the catalyst supply flow rate adjustment means may be a scheme that performs automatic control such that the concentration of acrylamide in the aqueous solution of acrylamide flowing out from the reaction product collecting pipe 27, and as necessary, the concentration of acrylonitrile are set to be in cooperation with the catalyst supply flow rate adjustment means so that the reaction rate from acrylonitrile to acrylamide is adjusted to a predetermined range.

In the invention, the concentration of acrylamide in the aqueous solution of acrylamide (flowing out from the reaction product collecting pipe 27) after the completion of reaction is preferably 30 to 65% by mass, more preferably 35 to 60% by mass, and still more preferably 40 to 55% with respect to the mass of the aqueous solution of acrylamide.

When the concentration of acrylamide is higher than 65% by mass, crystals of acrylamide easily precipitate near normal temperature, and thus a heating apparatus is required so that not only facility costs are increased but also temperature control and other operations are complicated. Therefore, the concentration of acrylamide in the aqueous solution of acrylamide in the invention is not particularly limited as long as it is within a range in which crystals of acrylamide do not precipitate even near normal temperature, and is preferably 65% by mass or less, more preferably 60% by mass or less, and most preferably 55% by mass or less.

On the other hand, when the concentration of acrylamide is lower than 30% by mass, it is economically disadvantageous from the industrial standpoint since the volume of a tank to be used for storage or keeping is excessively large or transport costs are increased. Therefore, the concentration of acrylamide in the aqueous solution of acrylamide is preferably 30% by mass or more, more preferably 35% by mass or more, and most preferably 40% by mass or more.

The concentration of unreacted acrylonitrile in the aqueous solution of acrylamide is preferably 200 ppm or less and more preferably 100 ppm or less.

When the concentration of unreacted acrylonitrile in the aqueous solution of acrylamide is adjusted to 200 ppm or less, the quality of an acrylamide-based polymer obtained by polymerization of acrylamide can be improved, and the above-described concentration range is industrially preferable since a conversion yield from acrylonitrile into acrylamide is high.

In order to adjust the concentration of unreacted acrylonitrile in the aqueous solution of acrylamide to 200 ppm or less, the supply amount or the like of the biocatalyst to be supplied to the reaction tank may be appropriately adjusted. For example, when the concentration of unreacted acrylonitrile in the aqueous solution of acrylamide collected by the reaction product collecting pipe 27 is higher than 200 ppm, the supply amount of the biocatalyst to be supplied to the reaction tank may be increased.

A biocatalyst supply port 29 in the catalyst supplying pipe 22 is preferably positioned in the vicinity of the stirring blade 24 in order that the concentration of the biocatalyst in the reaction tank 10 is not partially increased. However, the biocatalyst may be supplied from the upper portion of the reaction liquid surface.

(Stirring Blade)

The material of the stirring blade 24 is not particularly limited as long as it is not corroded by the reaction liquid and a predetermined stirring power can be obtained. As the material of the stirring blade 24, for example, stainless steel or the like is preferable. In addition, the stirring power will be described in the reaction condition to be described later.

The shape of the stirring blade 24 is not particularly limited, and for example, paddles, disc turbines, propellers, helical ribbons, anchors, Pfaudler stirrers, fan turbines, and the like are mentioned.

(Reaction Liquid Feeding Pipe)

The material of the reaction liquid feeding pipe 26 is not particularly limited as long as it is not corroded by the reaction liquid. Also, as the material of the reaction liquid feeding pipe 26, for example, stainless steel or the like is preferable.

The inner diameter of the reaction liquid feeding pipe 26 will be described in the section "Reaction Condition" to be described later.

The reaction liquid feeding pipe 26 is preferably inclined such that the upstream side of the reaction liquid becomes higher from the viewpoint of preventing retention of solid matters or the like of bacterial cells, which have produced enzyme, in the reaction liquid.

(Reaction Product Collecting Pipe)

The material of the reaction product collecting pipe 27 is not particularly limited as long as it is not corroded by the acrylamide-containing aqueous solution. As the material of the reaction product collecting pipe 27, for example, stainless steel or the like is preferable.

The inner diameter of the reaction product collecting pipe 27 is preferably 5 to 20 cm. When the inner diameter of the reaction product collecting pipe 27 is equal to or more than the lower limit, the collecting flow rate of the acrylamide-containing aqueous solution can be secured without requiring a large power for liquid feeding of the reaction liquid. On the other hand, when the inner diameter of the reaction product collecting pipe 27 is equal to or less than the upper limit, space saving is further achieved.

[Acrylonitrile-Containing Liquid]

The acrylonitrile-containing liquid is not particularly limited, and commercially available products may be used or produced products may be used. In order to decrease the consumption amount of the biocatalyst at the time of reaction, an acrylonitrile-containing liquid having a cyan concentration in acrylonitrile of 3 ppm or less is preferable.

The concentration of acrylonitrile in the acrylonitrile-containing liquid is preferably 90% by mass or more and more preferably 95% by mass or more with respect to the acrylonitrile-containing liquid.

When the concentration of acrylonitrile in the acrylonitrile-containing liquid is adjusted to 90% by mass or more, the amount of impurities in acrylonitrile is small and impurities in the aqueous solution of acrylamide produced by hydration of the acrylonitrile-containing liquid are also decreased. Thus, the quality of the aqueous solution of acrylamide is improved.

[Biocatalyst Aqueous Dispersion]

Biocatalysts include animal cells, plant cells, organelles, bacterial cells (live cells or dead cells), or treated products thereof that contain enzymes to catalyze target reactions. Examples of the treated products include raw or purified enzymes extracted from cells; and animal cells, plant cells, organelles, bacterial cells (live cells or dead cells), or enzymes themselves immobilized by using a comprehensive method, a crosslinking method, a carrier-binding method, or the like.

Herein, the comprehensive method is a method of wrapping bacterial cells or enzymes in a fine mesh of a polymer gel or coating bacterial cells or enzymes with semipermeable polymer membranes. In addition, the crosslinking method is a method of crosslinking enzymes using a reagent having two or more functional groups (polyfunctional crosslinking agent). Furthermore, the carrier-binding method is a method of binding enzymes to a water-insoluble carrier.

Examples of bacteria producing enzymes include microorganisms that belong to the genus *Nocardia*, the genus *Corynebacterium*, the genus *Bacillus*, the genus *Pseudomonas*, the genus *Micrococcus*, the genus *Rhodococcus*, the genus *Acinetobacter*, the genus *Xanthobacter*, the genus *Streptomyces*, the genus *Rhizobium*, the genus *Klebsiella*, the genus *Enterobavter*, the genus *Erwinia*, the genus *Aeromonas*, the genus *Citrobacter*, the genus *Achromobacter*, the genus *Agrobacterium*, and the genus *Pseudonocardia*.

Among them, microorganisms that belong to the genus *Rhodococcus* are preferable. The types of microorganisms that belong to the genus *Rhodococcus* are not limited, and for example, *Rhodococcus rhodochrous* J1 strain (Accession number: FERM BP-1478; internationally deposited to International Patent Organism Depositary, National Institute of Advanced Industrial Science and Technology (Chuo 6, Higashi 1-1-1, Tsukuba-shi, Ibaraki, Japan) on Sep. 18, 1987) and the like is more preferable.

As microorganisms used in the invention, not only the above-described microorganisms but also those subjected to genetic modification from those microorganisms can be used. There is no limitation on methods or types of genetic modification as long as a desired compound can be produced.

Enzymes are not particularly limited as long as they can produce a desired compound, and for example, a nitrile hydratase produced by the above-described microorganisms is preferable.

The used amount of the biocatalyst varies depending on the types or forms of the biocatalyst, but it is preferable that the activity of a biocatalyst to be introduced into a reaction vessel is adjusted to be about 50 to 500 U (unit) per 1 mg of dry bacterial cells at a reaction temperature of 10° C. Herein, the term "U (unit)" means enzyme activity to produce 1 μmol/l min of acrylamide from acrylonitrile, and represents a value measured by using acrylonitrile to be used in production.

The concentration of the biocatalyst in the biocatalyst aqueous dispersion is preferably 1 to 20% by mass and more preferably 5 to 15% by mass with respect to the biocatalyst aqueous dispersion.

When the concentration of the biocatalyst in the aqueous dispersion is adjusted to 1% or more, a volume of a biocatalyst aqueous dispersion storage tank 32 can be decreased and compactification of a production apparatus is achieved. On the other hand, when the concentration of the biocatalyst in the aqueous dispersion is adjusted to 20% or less, a viscosity of the biocatalyst aqueous dispersion can be suppressed, and a large quantity of energy is not required for liquid feeding. Thus, energy saving can be achieved.

Incidentally, the aqueous dispersion indicates an aqueous dispersion obtained by dispersing a biocatalyst in a solvent. As the solvent, water is exemplified. The same material as raw water may be used.

[Raw Water]

Raw water is used for hydration reaction with acrylonitrile when acrylamide is produced. Examples of raw water include water or aqueous solutions obtained by dissolving acids or salts in water. Examples of acids include phosphoric acid, acetic acid, citric acid, and boric acid. Examples of salts include sodium salts, potassium salts, and ammonium salts of acids described above. Specific examples of raw water include, although not particularly limited, water such as pure water, city water, and tap water; and buffer solutions such as a tris buffer solution, a phosphate buffer solution, an acetate buffer solution, a citrate buffer solution, and a borate buffer solution. The pH (at 25° C.) of the raw water is preferably 5 to 9.

The ratio of the acrylonitrile-containing liquid to the raw water which are supplied to the reaction tank is expressed as [volume of the acrylonitrile-containing liquid]/[volume of the raw water] and is preferably 0.4 to 1.2.

When a value of [volume of the acrylonitrile-containing liquid]/[volume of the raw water] is adjusted to 0.4 or more, the concentration of the aqueous solution of acrylamide produced by hydration of acrylonitrile can be easily adjusted to 30% or more. On the other hand, when a value of [volume of the acrylonitrile-containing liquid]/[volume of the raw water] is adjusted to 1.2 or less, the concentration of the aqueous solution of acrylamide produced by hydration of acrylonitrile can be easily suppressed to 65% or less.

A ratio of the acrylonitrile-containing liquid to the biocatalyst aqueous dispersion which are supplied to the reaction tank is expressed as [volume of the acrylonitrile-containing liquid]/[volume of the biocatalyst aqueous dispersion] and is preferably 50 to 800.

When a value of [volume of the acrylonitrile-containing liquid]/[volume of the biocatalyst aqueous dispersion] is adjusted to 50 or more, the used amount of the biocatalyst can be suppressed and deterioration of the quality of the aqueous solution of acrylamide caused by incorporating a large amount of impurities derived from the biocatalyst into the aqueous solution of acrylamide can be prevented. On the other hand, when a value of [volume of the acrylonitrile-containing liquid]/[volume of the biocatalyst aqueous dispersion] is adjusted to 800 or less, the used amount of the biocatalyst is decreased and the concentration of unreacted acrylonitrile in the aqueous solution of acrylamide can be suppressed to less than 200 ppm.

[Reaction Condition]

The method for producing acrylamide of this embodiment is performed in a state in which the Reynolds number of the reaction liquid flowing in the reaction liquid feeding pipe 26 is within a predetermined range. Further, the temperature of the reaction liquid in the reaction tank 10 and the stirring power are appropriately set.

(Reynolds Number)

In this embodiment, the Reynolds number of the reaction liquid flowing in the reaction liquid feeding pipe 26 is 1800 to 22000. The Reynolds number is preferably 2000 to 20000, more preferably 3000 to 15000, and still more preferably 5000 to 10000.

When the Reynolds number is equal to or more than the lower limit, the production efficiency of acrylamide can be improved. Moreover, since the prevention of retention of the reaction mixture in the reaction liquid feeding pipe 26, suppression of coloring of acrylamide, and prevention of polymerization of acrylamide, which is easily polymerized, are achieved, the quality of the produced acrylamide can be increased. On the other hand, when the Reynolds number is equal to or less than the upper limit, the liquid surface difference of the reaction liquid between the upstream reaction tank 10 and the downstream reaction tank 10 is further decreased, and the net reaction volume in the reaction tank 10 is further increased. Thus, the space saving of the continuous tank reactor 1 and improvement in reaction efficiency are achieved.

The Reynolds number (Re) is obtained by the following equation.

$$Re = V \times d \times \rho / \mu$$

Re: Reynolds number
V: Flow velocity (m/s) of the reaction liquid in the reaction liquid feeding pipe 26
d: Inner diameter (m) of the reaction liquid feeding pipe 26
ρ: Density (kg/m³) of the reaction liquid
μ: Viscosity (Pa·s) of the reaction liquid Herein, the density of the reaction liquid and the viscosity of the reaction liquid may vary depending on the temperature or the like of the reaction liquid, but since the optimal temperature of the biocatalyst is maintained, it is difficult to change the temperature of the reaction liquid largely so that it is difficult to artificially change the density of the reaction liquid and the viscosity of the reaction liquid largely. Therefore, in this embodiment, the Reynolds number of the reaction liquid flowing in the reaction liquid feeding pipe 26 is mainly adjusted by the flow velocity of the reaction liquid in the reaction liquid feeding pipe 26 and the inner diameter of the reaction liquid feeding pipe 26.

Incidentally, in general, the density of the reaction liquid is preferably 1.0 to 1.2 kg/m³, and the viscosity of the reaction liquid is preferably 1.5 to 5 Pa·s.

In the present specification, for the measurement of the density, methods of measurement using a pycnometer, measurement using a liquid weighing method, measurement using a hydrometer, measurement using an oscillator densitometer, and measurement using a magnetic levitation densitometer can be used. The viscosity can be measured by methods such as a capillary tube viscometer method and a rotating viscometer method.

Flow Velocity of Reaction Liquid in Reaction Liquid Feeding Pipe 26:

For adjustment of the flow velocity of the reaction liquid in the reaction liquid feeding pipe 26, a liquid feeding pump or a flow rate adjustment valve may be used or may not be used. When the liquid feeding pump is used, pressure energy is generated in the reaction liquid, and thus the flow velocity of the reaction liquid in the reaction liquid feeding pipe 26 can be increased. However, from the viewpoint of energy saving, space saving, cost suppression, and simplification of an apparatus, it is preferable that the flow velocity is adjusted without using the liquid feeding pump.

The flow velocity of the reaction liquid is preferably 0.1 to 1.5 m/s and more preferably 0.5 to 1.1 m/s.

Further, the flow rate can be measured by using a differential pressure flow meter, an electromagnetic flow meter, an area flow meter, an ultrasonic flow meter, an impeller flow meter, a thermal flow meter, a Coriolis flow meter, a volumetric flow meter, a vortex flow meter, a turbine flow meter, a pitot-tube flow meter, and the like. The flow velocity of the reaction liquid can be obtained by dividing the measured flow rate by a cross-sectional area of the reaction liquid feeding pipe 26.

In a case where the liquid feeding pump is not used, the flow of the reaction liquid from the upstream reaction tank to the downstream reaction tank is generated by using potential energy. Specifically, when the liquid surface of the upstream reaction tank is maintained to be higher than the liquid surface of the downstream reaction tank, the flow of the reaction liquid in the reaction liquid feeding pipe 26 toward the downstream direction is generated (see the dotted line of FIG. 1 and the liquid surface of each reaction tank 10).

The flow velocity of the reaction liquid in the reaction liquid feeding pipe 26 is further increased as the liquid surface difference is further increased, and the flow velocity thereof is further decreased as the liquid surface difference is further decreased. The liquid surface difference is appropriately controlled by adjusting the supply flow rate of the acrylonitrile-containing liquid to the reaction tank 11, the supply flow rate of the biocatalyst aqueous dispersion, the supply flow rate of the raw water, or the inner diameter of the reaction liquid feeding pipe.

In a case where reaction tanks having the same shape and the same internal capacity are used, when the downstream reaction tank is disposed at the position lower than that of the upstream reaction tank, the reaction volume in the reaction tank 10 can be further increased. Thus, space saving and improvement in reaction efficiency are further achieved.

In this embodiment, from the viewpoint of further achieving space saving, it is preferable that the liquid surface difference is further decreased and the reaction volume in the reaction tank 10 is further increased.

Specifically, the liquid surface difference between two reaction tanks directly connected to each other is preferably 0.05 to 10 cm, more preferably 0.08 to 5 cm, and still more preferably 0.1 to 3 cm.

Further, the liquid surface difference between the most upstream reaction tank and the most downstream reaction tank is preferably 0.1 to 80 cm, more preferably 0.3 to 50 cm, still more preferably 0.5 to 20 cm.

When the liquid surface difference is equal to or more than the lower limit, the reaction liquid can be fed from the upstream reaction tank 10 to the downstream reaction tank 10 by potential energy. Further, since the flow velocity of the reaction liquid in the reaction liquid feeding pipe 26 is increased and a sufficient Reynolds number can be obtained, the retention of the reaction liquid in the reaction liquid feeding pipe 26 can be suppressed. On the other hand, when the liquid surface difference is equal to or less than the upper limit, since the flow velocity is not increased too much and the Reynolds number is not increased too much, a sufficient reaction volume can be secured.

Inner Diameter of Reaction Liquid Feeding Pipe 26:

The reaction liquid feeding pipe 26 preferably has a cylindrical shape, and the inner diameter of the reaction liquid feeding pipe 26 is preferably 2 to 80 m, more preferably 3 to 50 m, and still more preferably 5 to 30 m. When the inner diameter of the reaction liquid feeding pipe 26 is equal to or more than the lower limit, a desired Reynolds number can be obtained without using pressure energy generated by the liquid feeding pump and the liquid surface difference can be further decreased. On the other hand, when the inner diameter of the reaction liquid feeding pipe 26 is equal to or less than the upper limit, the reaction volume in the reaction tank 10 can be further increased, and thus space saving and improvement in reaction efficiency are further achieved.

Incidentally, in a case where the reaction liquid feeding pipe 26 does not have a cylindrical shape, an equivalent diameter can be used as the inner diameter. The equivalent diameter can be calculated by the following calculation formula.

$$De = 4Af/Wp \ [m]$$

De: Equivalent diameter [m]
Af: Passage cross-sectional area [m$^2$]
Wp: Wetted perimeter length [m]

The inner diameter of the reaction liquid feeding pipe 26 with respect to the inner volume of the reaction tank 10 is preferably 3 to 30 cm/m$^3$ and more preferably 5 to 15 cm/m$^3$. When the inner diameter of the reaction liquid feeding pipe 26 with respect to the inner volume of the reaction tank 10 is equal to or more than the lower limit, a desired Reynolds number can be obtained without using pressure energy generated by the liquid feeding pump and the liquid surface difference can be further decreased. On the other hand, when the inner diameter of the reaction liquid feeding pipe 26 is equal to or less than the upper limit, space saving is further achieved.

(Temperature of Reaction Liquid)

The temperature of the reaction liquid is preferably 15 to 40° C. and more preferably 20 to 35° C. When the temperature of the reaction liquid is equal to or more than the lower limit, it is easy to sufficiently increase reaction activity of the biocatalyst. On the other hand, when the temperature of the reaction liquid is equal to or less than the upper limit, inactivation of the biocatalyst is prevented.

(Stirring Power)

The stirring power of the reaction liquid per unit volume by the stirring blade 24 is preferably 0.08 to 0.7 kW/m$^3$, more preferably 0.09 to 0.6 kW/m$^3$, and still more preferably 0.1 to 0.4 kW/m$^3$.

When the stirring power is equal to or more than the lower limit, the contact or dispersibility between acrylonitrile and the biocatalyst is improved and conversion efficiency from acrylonitrile into acrylamide is increased. Moreover, a reduction of the heat-transfer performance in the reaction tank 10 can be suppressed, temperature controllability of the reaction liquid is improved, and energy consumption of a cooler is decreased. On the other hand, when the stirring power is equal to or less than the upper limit, deterioration of the biocatalyst is suppressed, and catalyst reaction efficiency from acrylonitrile to acrylamide is increased.

Another Embodiment of Method for Producing Compound

[Compound Production System]

Hereinafter, as another embodiment of the method for producing a compound of the invention, a compound production system 2 will be described by means of FIG. 2.

Figure 2:
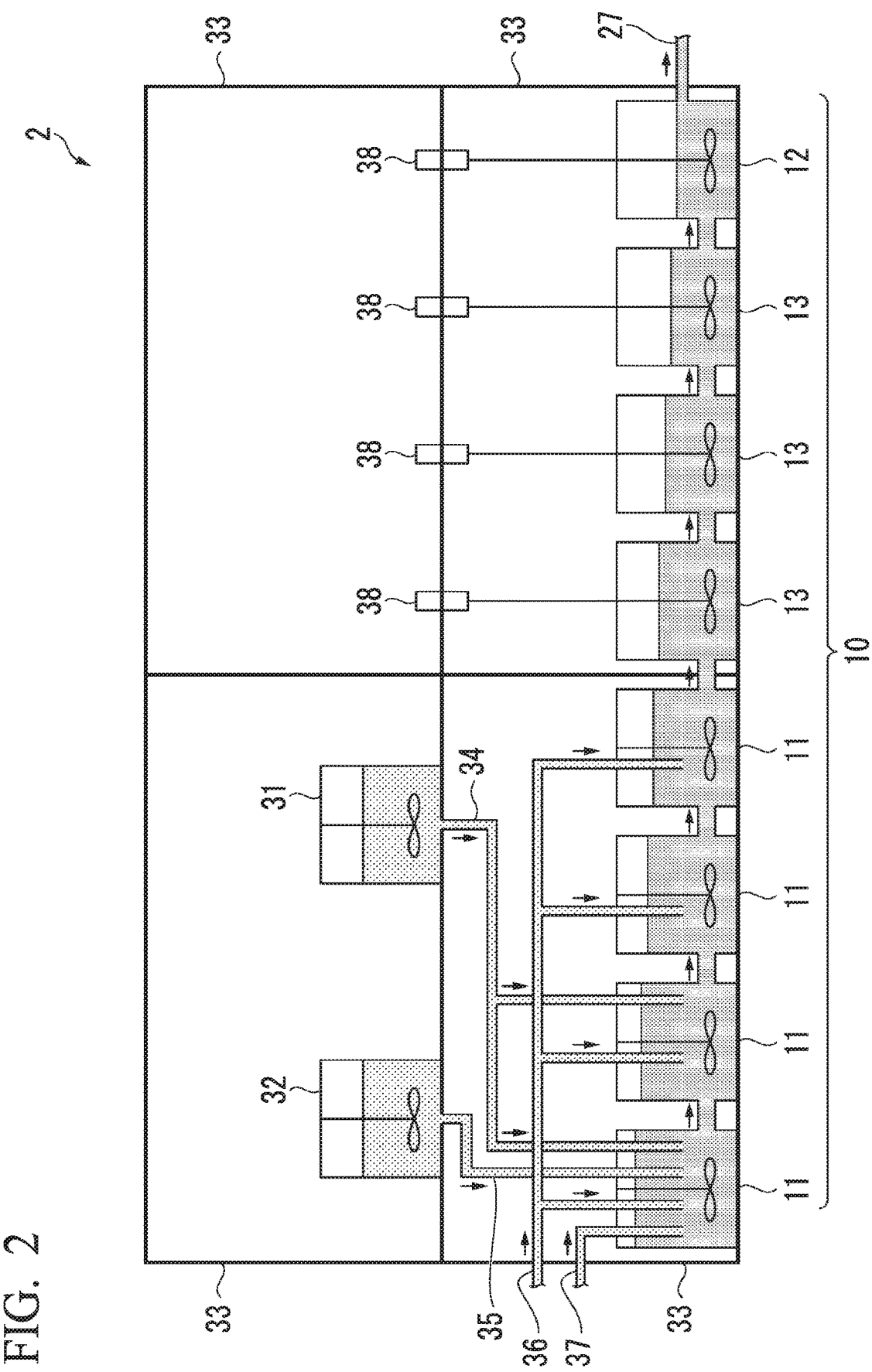
FIG. 2 is a schematic cross-sectional view illustrating another embodiment of a compound production system used in the method for producing a compound of the invention.

The production system 2 illustrated in FIG. 2 is provided with an alkali solution storage tank 31, a biocatalyst aqueous dispersion storage tank 32, a portable container 33, an alkali solution supplying pipe 34, a catalyst supplying pipe 35, an acrylonitrile supplying pipe 36, a raw water supplying pipe 37, and a motor 38, in addition to the configurations of the continuous tank reactor 1.

Incidentally, the same configurations in the production system 2 as the configurations of the continuous tank reactor 1 are the same as the embodiment of the aforementioned method for producing acrylamide, and thus the description thereof is omitted. Further, in FIG. 2, the same symbols as in FIG. 1 are given to the same configurations as the configurations illustrated in FIG. 1.

Hereinafter, the alkali solution storage tank 31, the biocatalyst aqueous dispersion storage tank 32, and the portable container 33 in FIG. 2 will be described in detail.

(Alkali Solution Storage Tank)

The alkali solution storage tank 31 is a tank storing an alkali solution used for controlling the pH of the reaction liquid in the reaction tank 10. In the embodiment of FIG. 2, the alkali solution to be stored in the alkali solution storage tank 31 is supplied to two reaction tanks 11 through the alkali solution supplying pipe 34.

The material of the alkali solution storage tank 31 is not particularly limited as long as it is not corroded by the alkali solution. The material of the alkali solution storage tank 31 is preferably, for example, stainless steel or the like.

The volume of the alkali solution storage tank 31 is appropriately set according to the process speed, but is preferably such a volume that enables each tank or two or more tanks to be accommodated in the portable container 33.

(Biocatalyst Aqueous Dispersion Storage Tank)

The biocatalyst aqueous dispersion storage tank 32 is a tank storing the biocatalyst aqueous dispersion. When acrylamide is produced, the biocatalyst aqueous dispersion to be stored in the biocatalyst aqueous dispersion storage tank 32 is fed to any of the reaction tanks 10 through the catalyst supplying pipe 35. In the embodiment of FIG. 2, the biocatalyst aqueous dispersion is supplied only to the most upstream reaction tank 10.

The material of the biocatalyst aqueous dispersion storage tank 32 is not particularly limited as long as it is not corroded by the biocatalyst. For example, stainless steel or the like can be used as the material of the biocatalyst aqueous dispersion storage tank 32.

The volume of the biocatalyst aqueous dispersion storage tank 32 is appropriately set according to the process speed, but is preferably such a volume that enables each tank or two or more tanks to be accommodated in the portable container 33.

(Portable Container)

The portable container 33 is used for accommodating and transporting the reaction tank 10, the alkali solution storage tank 31, and the biocatalyst aqueous dispersion storage tank 32. The portable container 33 is used, as necessary, for accommodating and transporting a purification apparatus of acrylamide.

The portable container 33 may accommodate any one or more tanks of the reaction tanks 10, the alkali solution storage tank 31, and the biocatalyst aqueous dispersion storage tank 32. It is preferable that the portable container 33 accommodates at least one tank of the reaction tanks 10.

Further, the volume of the reaction tank 10 to be accommodated in each portable container is preferably 6.4 $m^3$ to 22.9 $m^3$, more preferably 7.7 to 19.2 $m^3$, and still more preferably 11.5 to 15.3 $m^3$. When the volume of the reaction tank to be accommodated in the portable container is adjusted to 6.4 $m^3$ or more, production efficiency with respect to space can be further improved. When the volume of the reaction tank to be accommodated in the portable container is adjusted to 22.9 $m^3$ or less, effects of improving operability in the portable container and maintenance properties are obtained.

In a case where the reaction tanks 10 are accommodated in a plurality of portable containers, the volume of the reaction tank 10 means the volume of the reaction tank 10 in each portable container.

Further, in the compound production system 2 of this embodiment, only one portable container 33 may be provided or two or more portable containers 33 may be provided. In a case where two or more portable containers 33 are provided, the portable containers 33 may be horizontally arranged and used or be stacked and used when acrylamide is produced.

From the viewpoint of energy saving, it is preferable that the acrylonitrile-containing liquid, the biocatalyst aqueous dispersion, the reaction liquid, and the like are fed by using potential energy without using the liquid feeding pump. Form the viewpoint of space saving, it is preferable that the portable containers 33 are stacked and used as illustrated in FIG. 2. In addition, when the motor 38 rotating the stirring blade 24 is disposed in the stacked portable container 33 at the upper side, as compared to a case where the motor 38 is disposed directly on the reaction tank 10, the volume of the reaction tank 10 is easily increased and maintenance is easily performed.

The size of the portable container 33 is not particularly limited as long as it is a size in which any of the aforementioned tanks can be accommodated and transportation can be carried out, but a normalized portable container that can be transported by trailers, freight trains, ships, and the like is preferable. For example, a portable container normalized according to ISO 668 or the like is mentioned. Regarding the specific size, a portable container having a size of about 2.4 m (width)×about 2.9 m (height)×about 13 m (depth), and the like are exemplified, and as specific normalized examples, a 20 feet container, a 40 feet container, a 45 feet container, and the like are mentioned.

The volume of the reaction tank in each portable container 33 (the total volume of the plurality of reaction tanks in a case where a plurality of reaction tanks are accommodated in each portable container) is preferably ⅙ to ⅗ of the inner volume of each portable container 33 and more preferably ¼ to ½ of the inner volume of each portable container 33. When the volume of the reaction tank in each portable container 33 is equal to or more than the lower limit, production efficiency with respect to space is further improved. On the other hand, when the volume of the reaction tank in each portable container 33 is equal to or less than the upper limit, operation space can be sufficiently secured.

In production of acrylamide, the value obtained by dividing the inner volume ($m^3$) of the portable container by the flow rate ($m^3$/hour) of the reaction liquid flowing in the reaction tank accommodated in the portable container is preferably 5 to 70 hours and more preferably 15 to 65 hours. When the value is equal to or more than the lower limit, a more sufficient concentration of the acrylamide-containing aqueous solution is obtained, and the concentration of unreacted acrylonitrile in the obtained acrylamide-containing aqueous solution is further decreased. Thus, the quality of the acrylamide-containing aqueous solution is further improved. On the other hand, when the value is equal to or less than the upper limit, production efficiency with respect to space is further improved. Incidentally, the measurement method of the flow rate is as described above.

[Compound to be Produced]

The method for producing a compound of the invention is characterized in that when the Reynolds number of the reaction liquid flowing in the reaction liquid feeding pipe is set to be in a predetermined range, space saving is achieved without a decrease in production efficiency. Therefore, a compound to be produced by the method for producing a compound of the invention is not limited to the aforementioned acrylamide, and may be another compound which is known to be industrially produced.

The compound to which the method for producing a compound of the invention is applied is not particularly limited as long as it is a compound to be produced by chemical reaction, but a compound to be produced by chemical reaction in the presence of the biocatalyst is preferable.

Specific examples of a compound to be produced include amide compounds having an amide group in the molecule, and specifically, acryl compounds such as acrylamide, nicotinamide, 5-cyanovaleroamide, and methacrylamide are exemplified. In particular, acrylamide is preferable.

Examples of raw materials producing these compounds include acrylonitrile, 3-cyanopyridine, 1,4-dicyanobutane, and methacrylonitrile. In particular, acrylonitrile is preferable.

<Effect of Invention>

Hereinbefore, according to the invention, it is possible to provide a method for producing a compound using continuous reaction in which space saving is achieved without a decrease in production efficiency. Furthermore, a production system of the invention can be carried to a place in which there is a demand for using the production system and can start industrial production of a compound in a short time.

Since the reaction tank used in the method for producing a compound of the invention achieves space saving, that is, is decreased in size, the reaction tank can also be accommodated in the portable container. Then, the portable container can be transported by trailers, freight trains, ships, and the like while accommodating the reaction tank. For such reasons, the compound production system of the invention can be timely carried into a place in which there is a demand for using the compound production system and used, and in a case where there is no demand for using the compound production system, the compound production system can be carried to a next place in which there is a demand for using the compound production system.

Further, the compound production system is completed only by appropriately disposing the portable container while the reaction tank is accommodated in the portable container, and installing pipes between containers. For such a reason, when industrial production of a compound is started, since there is no need for fundamental construction in the installation of the continuous tank reactor, construction period can be shortened and construction costs are suppressed.

In the compound production system of the invention, when the portable containers accommodating the reaction tanks are stacked and used, space saving is also achieved.

When the portable container accommodating the tank positioned at the further upstream side in the reaction process is stacked at further upper side, the reaction liquid can be fed by using potential energy without using the liquid feeding pump, and thus energy saving is also achieved.

A person skilled in the art who will perform the method for producing a compound and does not have a reaction tank can newly dispose the continuous tank reactor or production system used in the method for producing a compound of the invention without requiring construction costs and construction period, and thus can perform the method for producing a compound of the invention. Further, a person skilled in the art who has already had the continuous tank reactor can properly expand or replace a reaction tank or a reaction liquid feeding pipe, and thus can perform the method for producing a compound of the invention.

EXAMPLES

Hereinafter, the invention will be described in more detail by means of Examples; however, the invention is not limited to these Examples.

Example 1

[Preparation of Biocatalyst]

*Rhodococcus rhodochrous* J1 strain having nitrile hydratase activity (Accession number: FERM BP-1478; internationally deposited to International Patent Organism Depositary, National Institute of Advanced Industrial Science and Technology (Chuo 6, Higashi 1-1-1, Tsukuba-shi, Ibaraki, Japan) on Sep. 18, 1987) was aerobically cultured in a medium (pH 7.0) containing 2% by mass of glucose, 1% by mass of urea, 0.5% by mass of peptone, 0.3% by mass of yeast extract, and 0.01% by mass of cobalt chloride hexahydrate at 30° C.

After cultivation, the obtained culture was subjected to harvest using a centrifuge. Then, the bacterial cells were suspended in 0.1% by mass of aqueous solution of sodium acrylate (pH 7.0) and the harvest and washing operation was performed five times by using a centrifuge again. Then, the bacterial cells were suspended in 0.1% by mass of aqueous solution of sodium acrylate (pH 7.0), thereby preparing a bacterial cell suspension containing 15% by mass of dry bacterial cells. The bacterial cell suspension was transferred to the biocatalyst aqueous dispersion storage tank in the portable container having a size of 2.5 m (width)×2.5 m (height)×6 m (depth) and was cooled to 5° C. until the following reaction, and then the bacterial cell suspension was used as the biocatalyst aqueous dispersion at the time of the following reaction.

[Reaction from Acrylonitrile to Acrylamide]

The reaction was performed by using a production system illustrated in FIG. 2.

Specifically, SUS reaction tanks having an inner volume of 2 m³ (1.3 m (width)×1.3 m (depth)×1.3 m (height)) were connected in series via a reaction liquid feeding pipe having an inner diameter of 5 cm and a length of 1 m, and the reaction was performed by using a continuous tank reactor in which a stirring blade (paddle type, blade diameter: 45 cm) was provided in each reaction tank. Four tanks of the reaction tanks were accommodated in each of two portable containers having a size of 2.5 m (width)×2.5 m (height)×6 m (depth) other than the portable container accommodating the aforementioned biocatalyst aqueous dispersion storage tank, and then the eight tanks were connected in series. The proportion of the reaction tanks (four tanks) in one container was set to 23%. The reaction tanks were designated as a first tank, a second tank, a third tank, a fourth tank, a fifth tank, a sixth tank, a seventh tank, and an eighth tank (hereinafter, the eighth tank is referred to as "most downstream reaction tank") from the upstream side of the reaction liquid.

The first tank was provided with the acrylonitrile supplying pipe, the raw water supplying pipe, the catalyst supplying pipe, and the alkali solution supplying pipe. The second tank was provided with the acrylonitrile supplying pipe and the alkali solution supplying pipe. The third tank and the fourth tank were provided with only acrylonitrile supplying pipe. The most downstream reaction tank was provided with the overflow type reaction product collecting pipe.

In this Example, the biocatalyst aqueous dispersion refrigerated in the biocatalyst aqueous dispersion storage tank in the portable container was supplied to the first tank through the catalyst supplying pipe.

In this Example, the alkali solution storage tank was also accommodated in the portable container accommodating the biocatalyst aqueous dispersion storage tank. Then, the alkali solution stored in the alkali solution storage tank was supplied to the first tank and the second tank through the alkali solution supplying pipe.

Further, the aqueous solution of acrylonitrile stored in the acrylonitrile storage tank disposed outside the portable container was supplied to the first tank to the fourth tank through the acrylonitrile supplying pipe.

Further, the raw water stored in the raw water storage tank disposed outside the portable container was supplied to the first tank through the raw water supplying pipe.

In this Example, 1.8 m³ of 50% by mass aqueous solution of acrylamide was introduced into the first tank to the seventh tank in advance before the start of the reaction.

The reaction was started by supplying the aqueous solution of acrylonitrile (concentration: 99.6% by mass, manufactured by MITSUBISHI RAYON CO., LTD.), the raw water, and the biocatalyst aqueous dispersion to the reaction tanks of the first tank to the fourth tank at the total supply flow ratio (the aqueous solution of acrylonitrile:the raw water:the biocatalyst aqueous dispersion) of 1.00:1.32:0.01. In this Example, the total of the flow rates of the aqueous solution of acrylonitrile, the raw water, and the biocatalyst aqueous dispersion was designated as a raw material supply amount. The raw material supply flow rate was adjusted such that the Reynolds number in each reaction liquid feeding pipe became 2000 to 2500.

The value obtained by dividing the inner volume (m³) of the portable container by the flow rate (m³/hour) of the reaction liquid flowing in the reaction tank accommodated in the portable container was set to about 50 hours.

During the reaction, 2% by mass of aqueous solution of sodium hydroxide was added from the alkali solution storage tank such that the pH of the reaction mixture in the first to fourth reaction tanks was adjusted to 7.0. The liquid feeding at the time of supplying the biocatalyst aqueous dispersion and 2% by mass of aqueous solution of sodium hydroxide was performed without using the liquid feeding pump by potential energy obtained by stacking the portable container accommodating the biocatalyst aqueous dispersion storage tank and the alkali solution storage tank on the portable container accommodating the first tank to the fourth tank. Further, the operation was performed such that the height of the liquid surface of the reaction liquid in the first tank occupied about 90% of the inner volume.

The reaction was performed under conditions including a reaction liquid temperature of 25° C. and a stirring power of 0.2 kW/m$^3$.

During the reaction, the liquid surface difference between reaction tanks of the first tank and the second tank was 5 mm or less.

Further, the flow rate of the aqueous solution of acrylamide flowing out from the overflow type reaction product collecting pipe during an hour from the start of the reaction under this condition was 99% or more of the raw material supply amount.

The concentration of acrylamide in the acrylamide-containing aqueous solution flowing out from the reaction product collecting pipe was measured by using a digital refractometer (manufactured by ATAGO CO., LTD.). Moreover, the concentration of unreacted acrylonitrile in the acrylamide-containing aqueous solution was measured by using gas chromatography (column: manufactured by Waters, PoraPack-PS, 1 m, 180° C., carrier gas: helium, detector: FID).

From the viewpoint of the quality of acrylamide, it is desirable that the concentration of acrylamide in the acrylamide-containing aqueous solution flowing out from the reaction product collecting pipe is 50% by mass or more and the concentration of unreacted acrylonitrile is less than 100 ppm.

In this Example, the concentration of acrylamide in the acrylamide-containing aqueous solution flowing out from the reaction product collecting pipe was 50.5% by mass, the concentration of acrylonitrile was 10 ppm or less, and it was possible to perform stable operation for three weeks or longer from the start of the reaction.

Example 2

An acrylamide-containing aqueous solution was collected in the same manner as in Example 1, except that the raw material supply flow rate was adjusted such that the Reynolds number of the reaction liquid flowing in each reaction liquid feeding pipe to 5000 to 5500, and then the concentration thereof was measured.

The value obtained by dividing the inner volume (m$^3$) of the portable container by the flow rate (m$^3$/hour) of the reaction liquid flowing in the reaction tank accommodated in the portable container was set to about 20 hours.

Incidentally, during the reaction, the liquid surface difference between the reaction tanks of the first tank and the second tank was 10 to 20 mm.

Further, the flow rate of the aqueous solution of acrylamide flowing out from the overflow type reaction product collecting pipe during an hour from the start of the reaction under this condition was 95% or more of the raw material supply amount.

In this Example, the concentration of acrylamide in the acrylamide-containing aqueous solution flowing out from the reaction product collecting pipe was 50.4% by mass, the concentration of acrylonitrile was 10 ppm or less, and it was possible to perform stable operation for three weeks or longer from the start of the reaction.

Example 3

An acrylamide-containing aqueous solution was collected in the same manner as in Example 1, except that the raw material supply flow rate was adjusted such that the Reynolds number of the reaction liquid flowing in each reaction liquid feeding pipe to 10000 to 11000, and then the concentration thereof was measured.

The value obtained by dividing the inner volume (m$^3$) of the portable container by the flow rate (m$^3$/hour) of the reaction liquid flowing in the reaction tank accommodated in the portable container was set to about 10 hours.

Incidentally, during the reaction, the liquid surface difference between the reaction tanks of the first tank and the second tank was 30 to 45 mm.

Further, the flow rate of the aqueous solution of acrylamide flowing out from the overflow type reaction product collecting pipe during an hour from the start of the reaction under this condition was 93% or more of the raw material supply amount.

In this Example, the concentration of acrylamide in the acrylamide-containing aqueous solution flowing out from the reaction product collecting pipe was 50.3% by mass, the concentration of acrylonitrile was 25 ppm, and it was possible to perform stable operation for three weeks or longer from the start of the reaction.

Example 4

An acrylamide-containing aqueous solution was collected in the same manner as in Example 1, except that the raw material supply flow rate was adjusted such that the Reynolds number of the reaction liquid flowing in each reaction liquid feeding pipe to 18000 to 20000, and then the concentration thereof was measured.

The value obtained by dividing the inner volume (m$^3$) of the portable container by the flow rate (m$^3$/hour) of the reaction liquid flowing in the reaction tank accommodated in the portable container was set to about 5 hours.

Incidentally, during the reaction, the liquid surface difference between the reaction tanks of the first tank and the second tank was 90 to 100 mm.

Further, the flow rate of the aqueous solution of acrylamide flowing out from the overflow type reaction product collecting pipe during an hour from the start of the reaction under this condition was 90% or more of the raw material supply amount.

In this Example, the concentration of acrylamide in the acrylamide-containing aqueous solution flowing out from the reaction product collecting pipe was 50.1% by mass, the concentration of acrylonitrile was 50 ppm, and it was possible to perform stable operation for three weeks or longer from the start of the reaction.

Comparative Example 1

An acrylamide-containing aqueous solution was collected in the same manner as in Example 1, except that the raw material supply flow rate was adjusted such that the Reynolds number of the reaction liquid flowing in each reaction liquid feeding pipe to 1000 to 1500, and then the concentration thereof was measured.

The value obtained by dividing the inner volume (m$^3$) of the portable container by the flow rate (m$^3$/hour) of the reaction liquid flowing in the reaction tank accommodated in the portable container was set to about 100 hours.

Incidentally, during the reaction, the liquid surface difference between the reaction tanks of the first tank and the second tank was 10 mm or less.

Further, the flow rate of the aqueous solution of acrylamide flowing out from the overflow type reaction product collecting pipe during an hour from the start of the reaction under this condition was 99% or more of the raw material supply amount.

In this Example, the concentration of acrylamide in the acrylamide-containing aqueous solution flowing out from the reaction product collecting pipe was 50.5% by mass, and the concentration of acrylonitrile was 10 ppm or less. However, after 3 days from the start of the reaction, settling of the biocatalyst occurred in the reaction liquid feeding pipe. Further, the aqueous solution of acrylamide flowing out from the reaction product collecting pipe was colored in faint yellow, and a small amount of a pop corn-like acrylamide polymer was mixed.

Comparative Example 2

An acrylamide-containing aqueous solution was collected in the same manner as in Example 1, except that the raw material supply flow rate was adjusted such that the Reynolds number of the reaction liquid flowing in each reaction liquid feeding pipe to 23000 to 25000, and then the concentration thereof was measured.

The value obtained by dividing the inner volume (m$^3$) of the portable container by the flow rate (m$^3$/hour) of the reaction liquid flowing in the reaction tank accommodated in the portable container was set to about 4 hours.

Incidentally, during the reaction, the liquid surface difference between the reaction tanks of the first tank and the second tank was 200 mm or more.

Further, the flow rate of the aqueous solution of acrylamide flowing out from the overflow type reaction product collecting pipe during an hour from the start of the reaction under this condition was 70% or less of the raw material supply amount. Further, the reaction liquid in the first tank reached 98% or more of the inner volume of the reaction tank.

Furthermore, the concentration of acrylamide in the acrylamide-containing aqueous solution flowing out from the reaction product collecting pipe was 49.5% by mass, and the concentration of acrylonitrile was 2000 ppm or more.

In this Comparative Example, the concentration of acrylamide and the concentration of acrylonitrile in the aqueous solution of acrylamide flowing out from the reaction product collecting pipe were not in the range that was desirable in terms of quality, and there was a concern that the reaction liquid of the reaction tank of the first tank might be overflowed. For such reasons, operation was stopped after an hour from the start of the reaction.

INDUSTRIAL APPLICABILITY

According to the invention, it is possible to provide a method for producing a compound using continuous reaction in which space saving is achieved without a decrease in production efficiency. Further, a production system of the invention can be carried to a place in which there is a demand for using the production system and can start industrial production of a compound in a short time.

EXPLANATIONS OF LETTERS OR NUMERALS

1. Continuous tank reactor;
2. Production system;
10 to 13. Reaction tank;
21, 36. Acrylonitrile supplying pipe;
22, 35. Catalyst supplying pipe;
23, 37. Raw water supplying pipe;
24. Stirring blade;
25. Acid/alkali solution supplying pipe;
26. Reaction liquid feeding pipe;
27. Reaction product collecting pipe;
28. Acrylonitrile supply port;
29. Biocatalyst supply port;
31. Alkali solution storage tank;
32. Biocatalyst aqueous dispersion storage tank;
33. Portable container;
34. Alkali solution supplying pipe; and
38. Motor

The invention claimed is:

1. A method for producing acrylamide in a continuous tank reactor, the method comprising:
   flowing a reaction liquid, which comprises acrylonitrile, a biocatalyst, and an acid or alkali solution from an upstream reaction tank to a downstream reaction tank via a reaction liquid feeding pipe at a Reynolds number of 2,000 to 20,000, wherein the continuous tank reactor comprises two or more reaction tanks, and the reaction liquid feeding pipe connects the upstream reaction tank to the adjacent downstream reaction tank, and a height of a liquid surface of the downstream reaction tank is lower than the height of the liquid surface of the upstream reaction tank,
   wherein the method produces acrylamide.

2. The method according to claim 1, wherein at least one tank of the reaction tanks is accommodated in a portable container, and a value obtained by dividing an inner volume (m$^3$) of the portable container by a flow rate (m$^3$/hour) of the reaction liquid flowing in the at least one reaction tank accommodated in the portable container is from 5 to 70 hours.

3. The method according to claim 1, further comprising:
   supplying an acrylonitrile-containing liquid to at least one tank of the reaction tanks;
   supplying raw water to at least one tank of the reaction tanks; and
   supplying a biocatalyst aqueous dispersion to at least one tank of the reaction tanks.

4. The method according to claim 1, further comprising:
   supplying an acrylonitrile-containing liquid, raw water and a biocatalyst aqueous dispersion to at least a tank positioned at the most upstream side of the reaction liquid.

5. The method of claim 1, wherein at least one tank of the reaction tanks is accommodated in a portable container, and wherein a total volume of the at least one tank accommodated in the portable container is $\frac{1}{6}$ to $\frac{3}{5}$ of an inner volume of the portable container.

6. The method of claim 1, wherein at least one tank of the reaction tanks is accommodated in a portable container, and wherein another portable container is disposed on the portable container in which the at least one tank of the reaction tanks is accommodated.

7. The method of claim 1, wherein at least one tank of the reaction tanks is accommodated in a portable container, and wherein a volume of the at least one reaction tank accommodated in the portable container is from 6.4 m$^3$ to 22.9 m$^3$.

8. The method of claim 1, wherein the liquid surface height difference between the reaction tank and the adjacent reaction tank is 0.05 to 10 cm.

9. The method of claim 1, wherein the liquid surface height difference between the reaction tank and the adjacent reaction tank is 0.1 to 3 cm.

* * * * *